(12) United States Patent
Guillama et al.

(10) Patent No.: US 11,121,877 B2
(45) Date of Patent: Sep. 14, 2021

(54) SECURE TRANSMISSION OF ELECTRONIC HEALTH RECORDS VIA BLOCKCHAIN

(71) Applicant: The Quantum Group Inc., Lake Worth, FL (US)

(72) Inventors: Noel J. Guillama, Wellington, FL (US); Chester Heath, Boca Raton, FL (US); Carl R. Larsen, West Palm Beach, FL (US)

(73) Assignees: The Quantum Group, Inc., Lake Worth, FL (US); Noel J. Guillama, Wellington, FL (US)

( * ) Notice: Subject to any disclaimer, the term of this patent is extended or adjusted under 35 U.S.C. 154(b) by 324 days.

(21) Appl. No.: 16/417,272

(22) Filed: May 20, 2019

(65) Prior Publication Data
US 2020/0374125 A1    Nov. 26, 2020

(51) Int. Cl.
| H04L 29/06 | (2006.01) |
| H04L 9/32 | (2006.01) |
| G16H 10/60 | (2018.01) |
| H04L 9/06 | (2006.01) |

(52) U.S. Cl.
CPC .......... H04L 9/3234 (2013.01); G16H 10/60 (2018.01); H04L 9/0637 (2013.01); H04L 9/0643 (2013.01); H04L 9/3297 (2013.01); H04L 2209/38 (2013.01)

(58) Field of Classification Search
CPC ... H04L 9/3234; H04L 9/0637; H04L 9/3297; H04L 9/0643; H04L 2209/38; H04L 63/123; H04L 9/3239; H04L 9/0894; H04L 2209/88; H04L 2209/56; G16H 10/60
See application file for complete search history.

(56) References Cited

U.S. PATENT DOCUMENTS

| 2009/0019516 | A1* | 1/2009 | Hammoutene | G06F 21/6245 726/1 |
| 2015/0332283 | A1* | 11/2015 | Witchey | H04W 12/02 705/3 |
| 2017/0103167 | A1* | 4/2017 | Shah | G06F 40/40 |
| 2017/0287068 | A1* | 10/2017 | Nugent | G06Q 20/065 |
| 2017/0300627 | A1* | 10/2017 | Giordano | G06F 21/6245 |
| 2018/0060496 | A1* | 3/2018 | Bulleit | H04L 9/3239 |
| 2018/0211058 | A1* | 7/2018 | Aunger | H04L 63/0428 |
| 2019/0354693 | A1* | 11/2019 | Yoon | G06F 21/6245 |
| 2019/0358515 | A1* | 11/2019 | Tran | A42B 3/0433 |
| 2020/0402629 | A1* | 12/2020 | Austring | H04L 9/3239 |

* cited by examiner

Primary Examiner — Harunur Rashid
(74) Attorney, Agent, or Firm — Nixon Peabody LLP (57) ABSTRACT

The present disclosure provides a method for securely transmitting electronic healthcare records between computing devices in communication. A request is received to access a database of electronic health records, checking for an authorization requirement, and generating a token associated with the authorization requirement and the received request. The token corresponds to a block in a Blockchain. The block includes a cryptographic hash of a previous block, a timestamp, and transaction data related to the received request, and the at least one authorization requirement. The token can be sent to allow access to at least one electronic health record in the database of electronic health records.

12 Claims, 7 Drawing Sheets

SECURE TRANSMISSION OF ELECTRONIC HEALTH RECORDS VIA BLOCKCHAIN

FIELD

The present disclosure relates to securely transmitting and accessing electronic healthcare records.

BACKGROUND

In a conventional healthcare system, many doctors, nurses, and other healthcare professionals typically do not use digital communication to coordinate patient care or keep patient records. Often, healthcare professionals rely on written legers, file folders, copiers, fax machines, and telephones. These isolated sources of data are rarely integrated into an electronic file at the healthcare professional's location of business. Even when a patient requests his or her healthcare record from the professional, some sources of data may be missing or omitted because the isolated sources were never integrated.

In addition to the hassle of integrating written files into an electronic system, laws heavily regulate the sharing and protections surrounding electronic healthcare data. Few conventional electronic systems can provide the rigorous security requirements. Therefore, even if some paper records are converted to electronic health records, most of these conventional electronic health records are only used internally within a healthcare professional's business; the electronic records are converted to paper records for transfer. Consequently, many healthcare professionals find that electronic health systems reduce clinical efficacy instead of enhancing it.

Additionally, in an age of constant data breaches, patients are wary of electronically securing or transferring health records. A patient's health record is a uniquely private collection of personal data, and conventional electronic databases do not provide rigorous enough security to assuage consumer fears of data breach.

Therefore, what is needed is a way to combine and transfer databases in a secure manner.

SUMMARY

The various examples of the present disclosure are directed towards a method for securely transmitting electronic healthcare records between computing devices in communication with each other. The method can include receiving, at a first computing device, a request from a second computing device to access at least one electronic health record in a database of electronic health records. The database of electronic health records can be stored at a remote memory module. The method can also include sending, from the first computing device, at least one authorization requirement to the second computing device. The method can include detecting, at the first computing device, that the at least one authorization requirement has been provided by the second computing device. Based on detecting that the at least one authorization requirement has been provided, the method includes generating, at the first computing device, a token associated with the at least one authorization requirement and the received request. The token can correspond to a block in a Blockchain. The block can include a cryptographic hash of a previous block, a timestamp, and transaction data related to the received request, and the at least one authorization requirement. The method can also include sending the token to the second computing device from the first computing device to access the at least one electronic health record.

In some embodiments, the at least one authorization requirement includes a payment request based on the received request. In some embodiments, detecting that the at least one authorization requirement has been provided includes receiving, at the first computing device, a payment from the second computing device. The payment corresponds to the payment request. In some embodiments, the method can include sending, via the first computing device, the payment to a user associated with the at least one electronic health record. In some embodiments, each electronic health record in the database of electronic health records is automatically generated upon receiving health information from a user. In some embodiments, generating each electronic health record is based on the received health information and includes access restrictions. In some embodiments, the database of electronic health records comprises de-identified data accessible by the computing devices. In some embodiments, the request from the second computing device is based on accessing de-identified data of the at least one electronic health record.

In some embodiments, the method can also include additional steps. The claimed method can include retrieving, by the first computing device, identifiable data from the remote memory module. The identifiable data corresponds to the received request. The method can include encrypting, by the first computing device, the identifiable data. The method can also include sending, from the first computing device, the encrypted identifiable data to the second computing device.

In some examples of the first embodiment, the token provides a decryption key for the encrypted identifiable data.

A second embodiment of the present disclosure provides for a system for securely transmitting electronic healthcare records between a plurality of computing devices in communication with each other. The system includes one or more processors, and a memory coupled to the processors comprising instructions executable by the processors. The processors are operable, when executing the instructions, to perform the steps of the method provided for by the first embodiment, detailed above. Additional embodiments of the second embodiment can be similar to those provided above.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims.

BRIEF DESCRIPTION OF THE DRAWINGS

The accompanying drawings exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

DETAILED DESCRIPTION

The present invention is described with reference to the attached figures, where like reference numerals are used throughout the figures to designate similar or equivalent elements. The figures are not drawn to scale, and are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details, or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The present disclosure is directed to systems and method for electronically transferring and accessing healthcare records. Patients, who correspond to the healthcare records, can be incentivized to share their electronic healthcare records with health care providers, research institutions, or other parties. The disclosed system and methods provide rigorous protection of the electronic records during storage and transmission of the records. Therefore, the present disclosure enables widespread use of credit identification and monetary transfer with computers enabled automatic attendants and tellers. Altogether, the present disclosure provides trust, accuracy, and security for health records. The disclosed system and methods also provide comprehensive data protection as required by local laws and regulations.

Figure 1A:
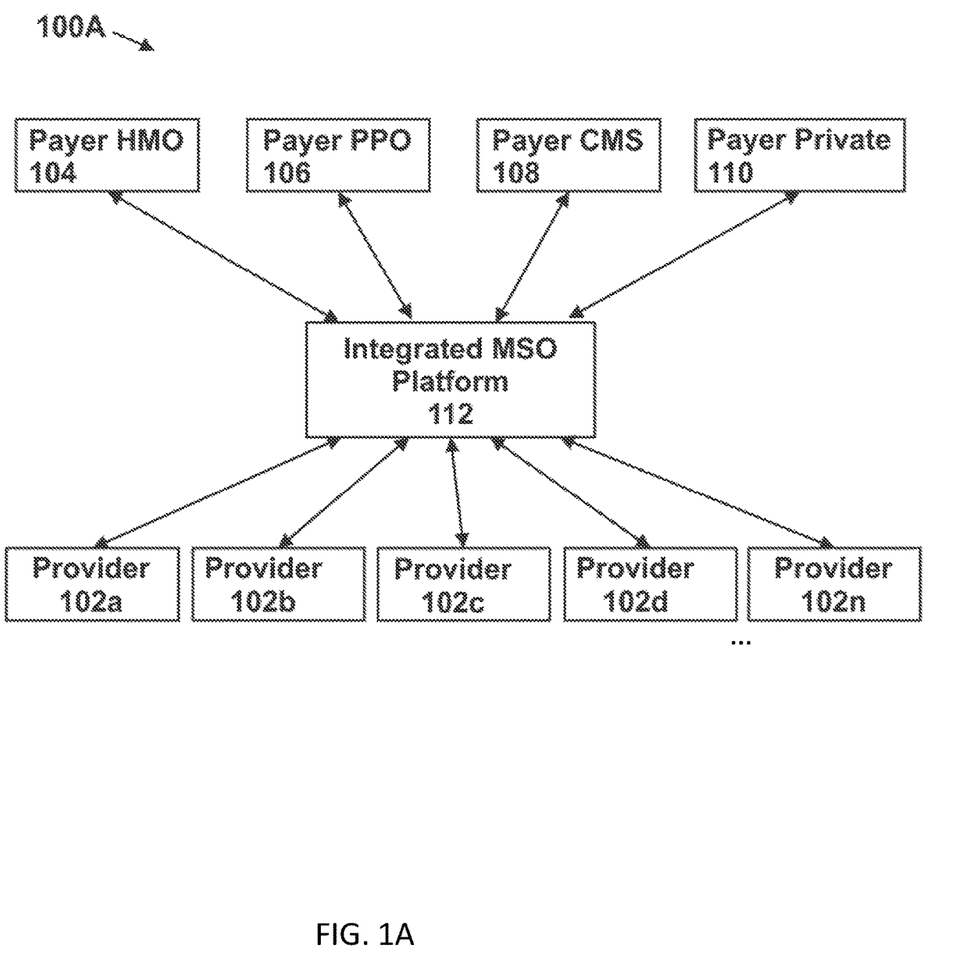
FIG. 1A shows a conventional system for providing integrated health record management, according to prior art.

FIG. 1A shows a conventional system 100A for providing integrated health record management, as generally understood. System 100A includes providers 102a, 102b, 102c, 102d . . . 102n. The system 100A also includes a health maintenance organization (HMO) payer 104, a preferred provider organization (PPO) payer 106, a center for Medicare and Medicaid services (CMS) payer 108, a private payer 110, and an integrated managed services organization (MSO) platform 112.

The MSO platform 112 provides common services to the multiple providers 102a, 102b, 102c, 102d . . . 102n and payers 104, 106, 108, 110. In some conventional examples, the MSO platform 112 is a legally compliant intermediary (e.g., compliant with HIPAA regulations) where various HMO, PPO, and CMS platforms are serviced by a common foundation, the MSO platform 112. In this exemplary health record exchange and storage system 100A, providers 102a, 102b, 102c, 102d . . . 102n submit claims, through the MSO platform 112 to the payers 104, 106, 108, 110. The MSO platform 112 requires staffing of trained specialists and continuous security, and constant security overview by system employees. These employees overseeing the MSO platform 112 additionally reviewed claims submitted by the providers 102a, 102b, 102c, 102d . . . 102n to determine whether the claim was properly submitted and payable.

However, the MSO platform 112 requires upkeep from employees and does not provide an autonomously functioning electronic healthcare system.

Figure 1B:
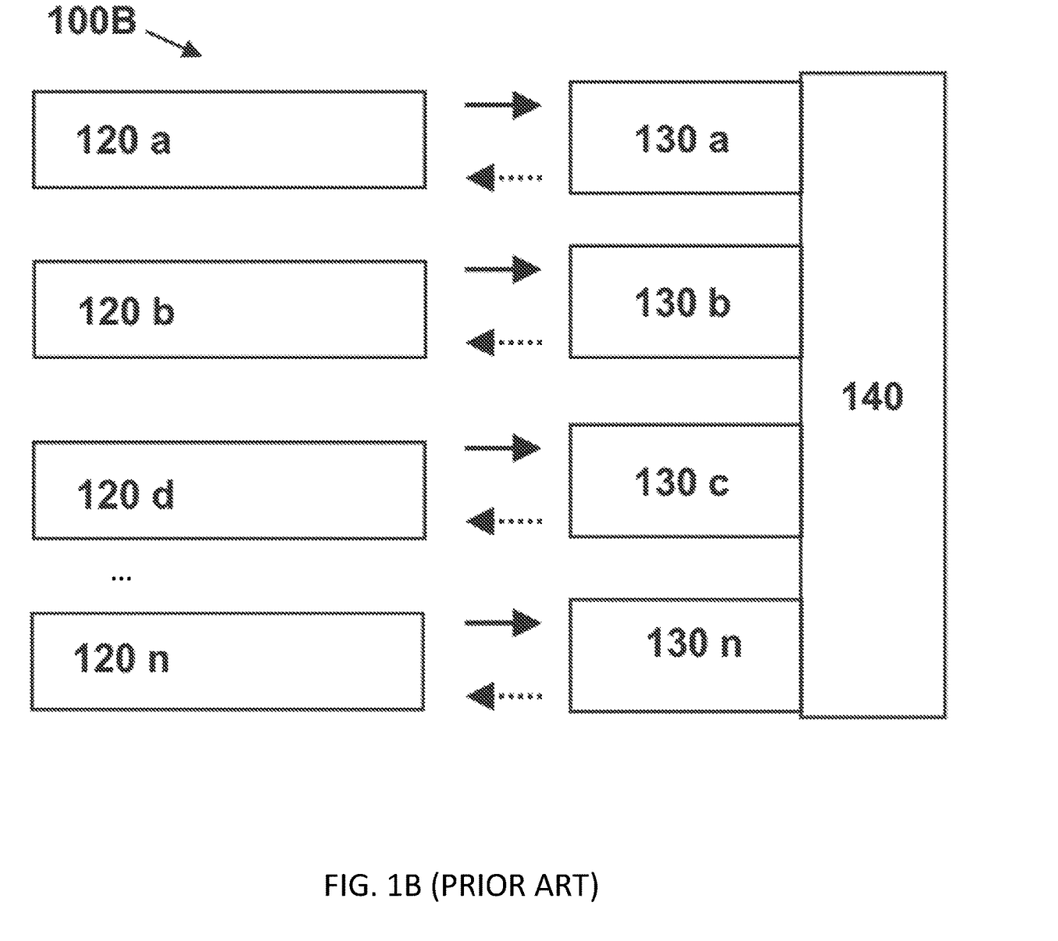
FIG. 1B shows another conventional system for providing integrated health record management, according to prior art.

FIG. 1B shows another conventional system 100B for providing integrated health record management, as generally understood. System 100B includes data customers 120a, 120b, 12c . . . 120n. The system 100B also includes paying research organizations 130a, 130b, 130c . . . 130n, and an intermediary organization 140. The intermediary organization 140 provides support for the paying research organizations 130a, 130b, 130c . . . 130n to request access to electronic records from the data customers 120a, 120b, 12c . . . 120n. In some examples, the intermediary organization 140 filters incoming requests from the paying research organizations 130a, 130b, 130c . . . 130n to assign the requests to particular data customers 120a, 120b, 12c . . . 120n.

System 100B offers similar security advantages as system 100A above. The intermediary organization 100B must expend significant resources in continuous training, security, and staffing of those who manage the database. Additionally, no integrated system exists which can provide for submitting payment claims (system 100A) and handling research requests (system 100B).

Figure 2:
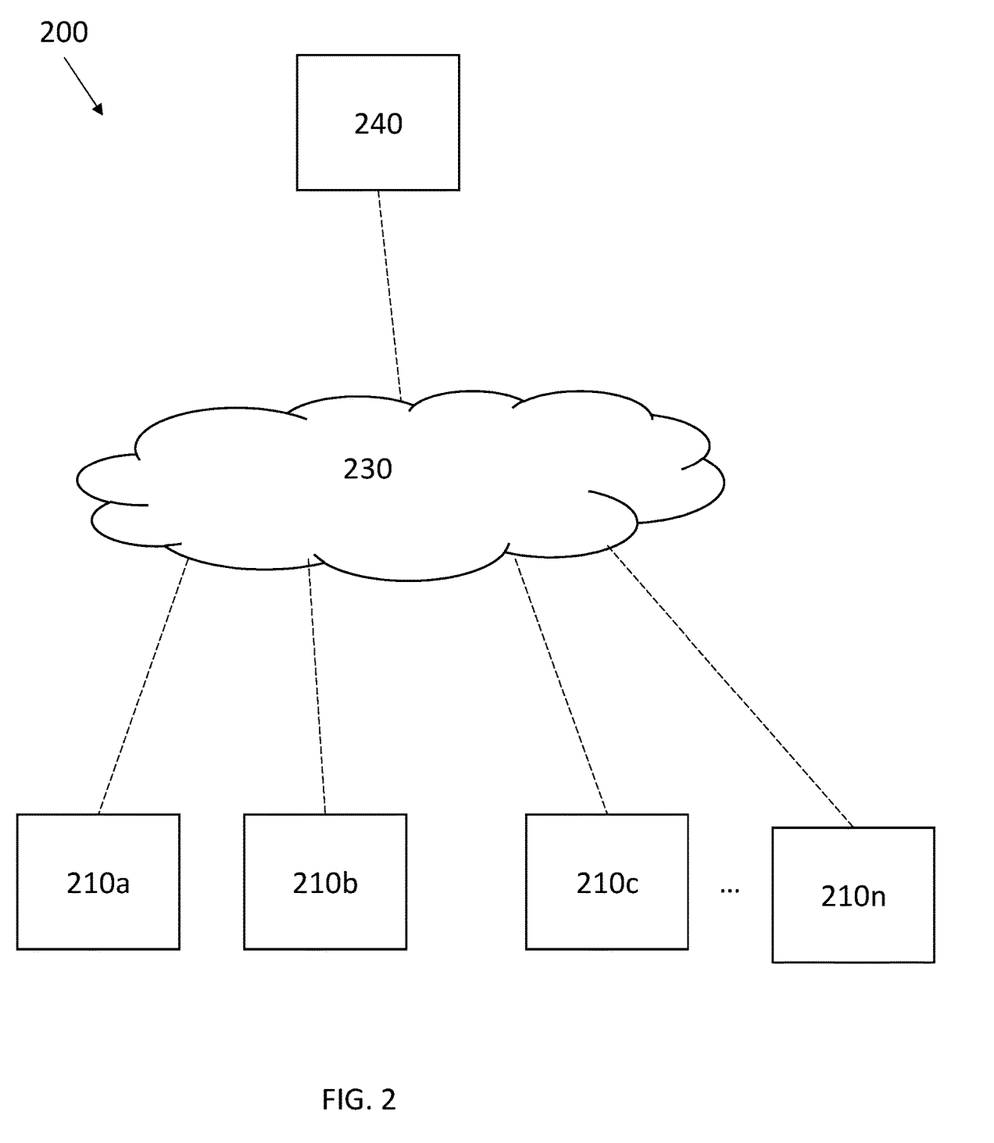
FIG. 2 shows an exemplary system for securely transmitting and accessing electronic health records, according to an embodiment of the present disclosure.

In response to the limitations of the aforementioned systems, the present disclosure provides systems and methods for securely transmitting and accessing electronic health records. FIG. 2 shows an exemplary system 200, according to an embodiment of the present disclosure. System 200 includes computing devices 210a, 210b, 210c . . . 210n connected to a remote computing device 240 via network 230.

The computing devices 210a, 210b, 210c . . . 210n are communicatively coupled to each other, for example, by wired or wireless connections. The computing devices 210a, 210b, 210c . . . 210n are additionally communicatively coupled to a network 230. In some examples, the network 230 provides the communicative coupling between the computing devices 210a, 210b, 210c . . . 210n. For example, the network 230 facilitates communication between the computing devices 210a, 210b, 210c . . . 210n as provided for in method 300, discussed below with respect to FIG. 3. The computing devices 210a, 210b, 210c . . . 210n can be associated with users, providers, or payers. Each computing device 210a, 210b, 210c . . . 210n can be associated with a particular user.

The remote computing device 240 hosts a database of electronic health records. The remote computing device 240 allows computing devices 210a, 210b, 210c . . . 210n restricted access to the database of electronic health records. For example, the access can be restricted as provided for below with respect to method 300 of FIG. 3.

Figure 3:
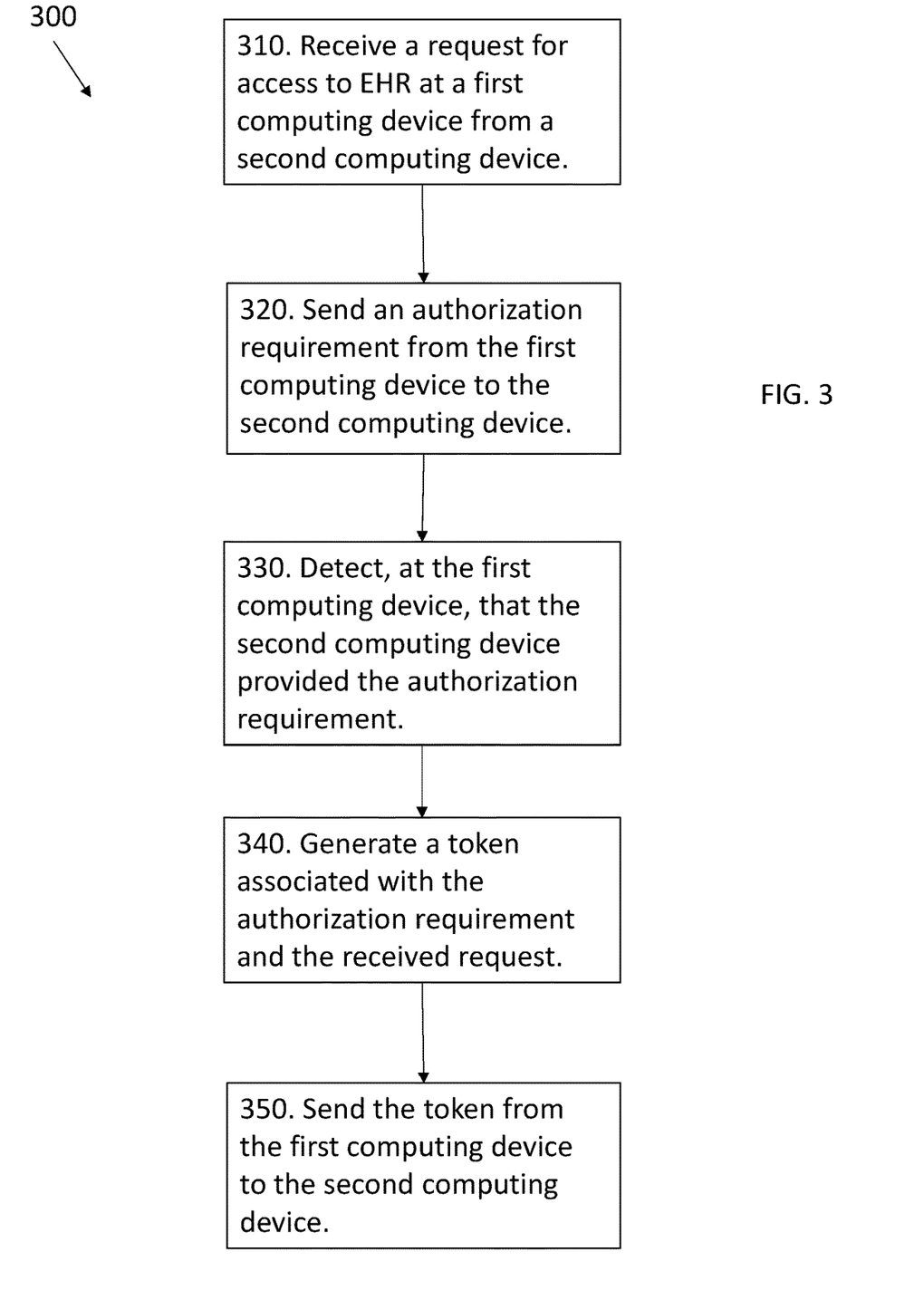
FIG. 3 shows an exemplary methodology for securely transmitting and accessing electronic health records, according to an embodiment of the present disclosure.

Turning now to FIG. 3, the present disclosure provides a methodology 300 for securely transmitting and accessing electronic health records. The methodology 300 is described in detail with respect to the components detailed in the system 200.

Methodology 300 begins at step 310, where a request is received at a first computing device from a second computing device to access at least one electronic health record in a database of electronic health records. The first and second computing device can include any of the computing devices 210a, 210b, 210c . . . 210d of FIG. 2. The database of electronic health records can be stored at a remote memory module. The remote memory module can correspond with the computing device 240 of FIG. 2.

In some embodiments, each electronic health record in the database of electronic health records can be automatically generated upon receiving health information from a user. In some embodiments, these generated electronic health records can be based on the received health information and include access restrictions.

In additional embodiments, the database of electronic health records can include de-identified data accessible by the computing devices.

Furthermore, in some embodiments, the request from the second computing device can be based on accessing de-identified data of the at least one electronic health record.

In some embodiments, the first computing device can be associated with a patient and the second computing device can be associated with a second entity interested in accessing the patient's record. For example, the second entity can be the user himself, an external research organization, another healthcare professional, or any other party as contemplated by one skilled in the art.

At step 320, at least one authorization requirement is sent, from the first computing device, to the second computing device. In some embodiments, the authorization requirement can include a payment request based on the received request.

For example, a patient can be associated with the first computing device, and a research organization can be associated with the second computing device. Step 320 of the methodology 300 provides a patient the ability to authorize release of their electronic health record (stored at the remote computing device). In some embodiments, the access can be restricted to de-identified data. The present disclosure also notes that the authorization requirement can allow access to any combination of: (1) historical data only, (2) historical, and, for all future time, future updates of the historical data, and (3) historical data and/or future updates of the historical data for a designated period. This process provides preselected levels of security.

At step 330, the first computing device can detect whether at least one authorization requirement has been provided by the second computing device. In some embodiments, this can include receiving, at the first computing device, a payment from the second computing device. The payment can correspond to the payment request. In some embodiments, the first computing device can send the payment to a user associated with the electronic health record.

Thereby, the methodology 300 enables patients to be paid for their healthcare data. Furthermore, participating patients are able to receive an incentive for allowing researchers access to their de-identified medical information. This process provides for compensating patients for the use of their personal health information.

At step 340, a token can be generated based on detecting that the authorization requirement has been provided. The token can be associated with the authorization requirement and the received request. The token can also correspond to a block in a Blockchain. In some embodiments, the block can include a cryptographic hash of a previous block, a timestamp, and transaction data related to the received request, and the at least one authorization requirement. In some embodiments, the token can provide a decryption key for the encrypted identifiable data.

In some examples of step 340, the generated token can be an unencrypted unique number or value. For example, in secured, enclosed computing environments, encryption is not needed for transactions within the computing environment (e.g., system 200 can be a completely secured environment where computing devices 210a, 210b, 210c . . . 210n communicate with each other without encryption).

In some examples of step 340, the generated token can be a payment amount. In some examples of step 340, the generated token is encrypted by any other encryption method, as known in the art.

At step 350, the token can be sent to the second computing device from the first computing device to access the at least one electronic health record. The compensation structure described above with respect to step 320 enables researchers to work within a HIPAA compliant environment (and a technologically secure environment), while exporting the collective, de-identified data afterwards in step 350. For example, this can be referred to as a Personal Wellness Blockchain Record Electronic Health Record.

Additional steps can be included in methodology 300. For example, identifiable data can be retrieved from the remote memory module by the first computing device. The identifiable data can correspond to the received request. The identifiable data can be encrypted by the first computing device. The encrypted identifiable data can be sent from the first computing device to the second computing device.

In one embodiment of methodology 300, a computing device associated with a research organization accesses de-identified data corresponding to patients, the de-identified data hosted in the electronic database of records at the remote computing device. De-identified data corresponds to data which is not identifiable as associated with a particular patient. For example, identifiable data can have a user's name, date of birth, address, phone number, or other identifiable characteristics stripped from the data before other users are permitted to view the records. The present disclosure contemplates that various levels of de-identification can be provided for at varying stages in the methodology 300, as readily contemplated by one skilled in the art. For example, data can be fully or partially identifiable at step 350 after payment and authentication has been verified. In some embodiments, data is fully de-identifiable at step 310; particular characteristics are added back in at step 350 when the record is transferred, but the data still omits particularly identifiable fields (e.g., name, address, phone number). In some embodiments, a patient can allow access to increasing amounts of their associated electronic health records based on compensation offered by another entity.

In some embodiments of method 300, a patient at a second computing device requests access to his own electronic health record. For example, the patient can be in a location separate from where the electronic health record originated. These different locations can include different doctor offices.

Method 300 further provides patients the ability to track who and what type of organization is accessing their information.

Methodology 300, as such, provides a large amount of data, available real-time, continuously, across any number of users. In some embodiments, the disclosed systems and methods revolutionize clinical trials by readily providing access to electronic health records for research across the globe. In other embodiments, exemplary systems and methods in accordance with methodology 300 securely connect Internet of Things (IoT) devices and smart phones.

In some embodiments of method 300, insurers aggregate claims data by accessing the patient's de-identified claim history. By adding claim history, the patients' profiles have more valuable information available for researchers.

Methodology 300, therefore, provides a verifiable system for transferring and accessing health records. The exemplary Blockchain database (as discussed with respect to step 340) provides a self-contained, private network, and, in some examples, provides a thoroughly de-identified system with Blockchain integrity. Additional embodiments and enablement of Blockchain methodology are discussed further below. Methodology 300 additionally enables a collaborative opportunity for both public and private applications for Blockchain use in healthcare by integrating management of identified and de-identified data into a common system.

Figure 4A:
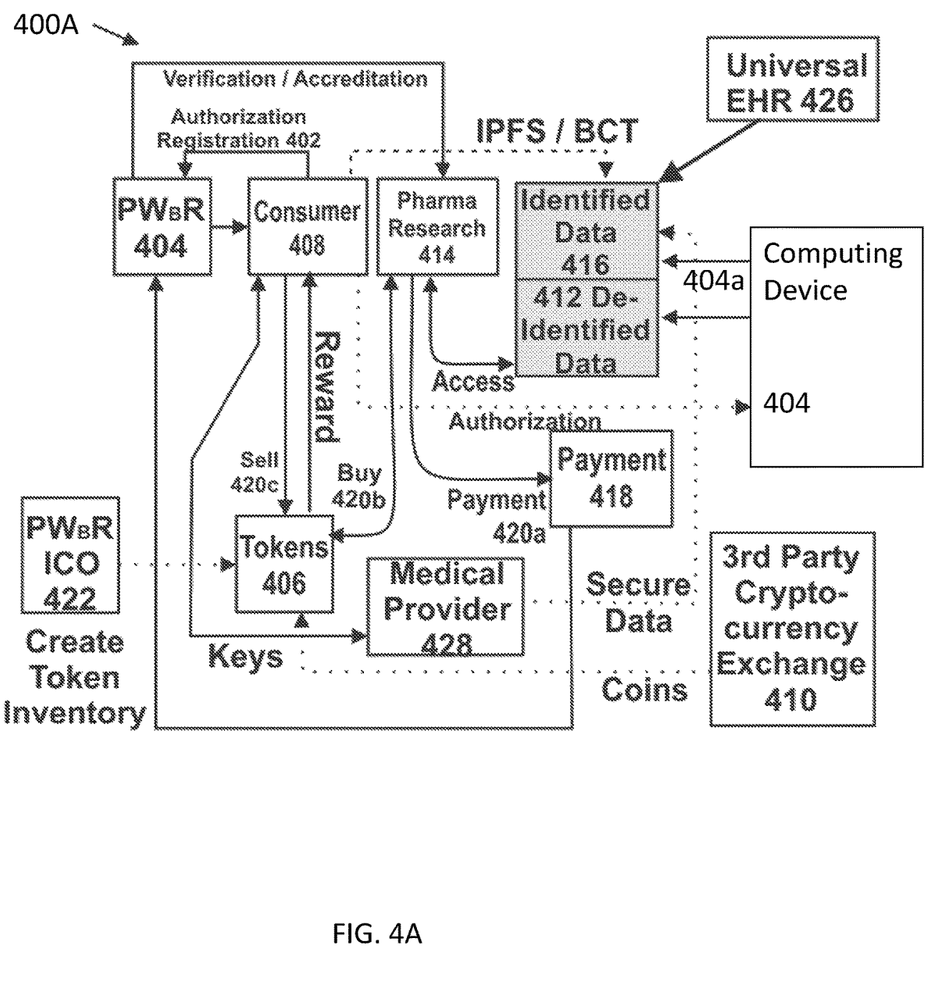
FIG. 4A shows an exemplary implementation of the methodology of FIG. 3, according to an embodiment of the present disclosure.

FIG. 4A shows an exemplary system 400A implementing the methodology of FIG. 3, according to an embodiment of the present disclosure. System 400A can be interacted with by one or more consumers 408 and one or more accredited users 414. Additional details of the interactions are discussed in further detail below.

At step 402, a consumer 408 opens an account at a remote computing device 404. This remote computing device 404 can hold a plurality of electronic records. Opening the account at step 402 can include opening, via a third party 410, a cryptocurrency exchange for deposit of tokens 406. At step 402, the consumer 408 loads, enters, and/or scans both biographical and clinical information. In some embodiments, the entry can be performed at step 404a, where the entry yields de-identified data 412 and identified data 416. Other health information can be provided by the consumer 408 as well, without limitation. This registration step 402 further provides permission to the remote computing device 404 to connect to other health information systems via a personal portal and import information, as readily contemplated by one skilled in the art. This new account can be compiled as a new electronic health record 426 (including both identifiable data 416 and de-identifiable data 412) and can be stored in master file. In some examples, the storage can be at the remote computing device 404, or at any other remote location.

In some embodiments, the consumer 408 can manually enter healthcare data at step 404a. In some examples, step 404a accepts information from mobile phones, tables and desktops.

In some embodiments, the consumer 408 chooses which information to upload (at step 402/404a) from a pre-filled electronic health record. In some embodiments, the consumer 408 individually approves each data entry before the information is permanently appended to the consumer's secure electronic health record 426.

Therefore, step 402 allows de-identified healthcare information 412 to be marketed to accredited users 414. Accredited users 414 can be screened and verified by the electronic database 404 to determine whether the accredited users 414 have provided the proper authentication requirements. For example, the remote computing device 404 provides qualification for research purposes only. Accredited users 414 can include pharmaceutical companies, government health agencies, universities, insurance institutions, and other organizations dealing with healthcare information.

An accredited user 414 sees or collects files or metadata that includes consumer data (e.g., identified data 416, or in some cases, partially de-identified data); the accredited user 414 pays a certain amount 418 for the access of this information (e.g., data 416). This payment 418 can be provided for by tokens 406, and the payment process 420a can be done in the open using a Blockchain and token. Consumers 408 can also sell (e.g., at step 420c) the tokens 406, and the accredited user 414 can buy (e.g., at step 420b) the tokens 406.

These tokens 406 can be issued as part of an Initial Coin Offering 422, as known in the art. The tokens 406 therefore provide sufficient liquidity to support commerce between the accredited users 414 and the consumers 408. In some embodiments, at step 424, an accredited user 414 buys tokens 406 in an open market, such as the cryptocurrency exchange 410, at market prices and using a Blockchain.

After the payment transaction by the accredited user 414, the consumer 408 receives a portion of the payment 418. In some examples, a portion of the payment 418 is retained by the remote computing device 404 for operating costs and profit. The payment 418 is transmitted to the consumer 408 via tokens 408, or by using the open currency exchange 410. A consumer 408 can thereafter (1) convert the tokens 408 to a preferred currency, (2) hold the funds at the remote computing device 404, or (3) transfer the funds to a local bank or financial institution that would be handled by unrelated parties.

In some examples of 404a, a consumer 408 enters personal health information through a template.

Altogether, universal healthcare record 426 provides a profile report of each consumer 408. It contains the type of information available, using encounter and treatment data based on contemporary healthcare codes, along with provider taxonomy classifications, as known in the art. The more universal healthcare records 426 that are available from consumers 408, the more valuable the information will be and the more tokens will be generated due to data exchange.

In some embodiments of system 400A, accredited users 414 can request additional data from the consumers 408; the additional data, such as identifiable data 416, can be requested through an anonymous interface provided by the remote computing device 404. Consumers 408 can choose to approve or deny this supplementary request. In some examples, the request may be for additional data not already provided in the universal health care record 426; in such a case, the consumer 408 can enter additional data at step 404a in response to the supplementary request. This supplementary request can be authorized according to step 402, as discussed above.

In some examples, this additional information (and the original information as discussed with respect to steps 402 and 404a above) can be collected as digitally segregated information, uploaded in a PDF format, or in any other electronic transfer protocol, as known in the art. Information can be both structured and unstructured. Information can be integrated from existing universal health records 426, from acute systems, ancillary providers, or ambulatory care systems, as known in the art. The integration can be dependent on the consent of the consumer 408 and the completion of a proper access authorization of the request 402.

Figure 4B:
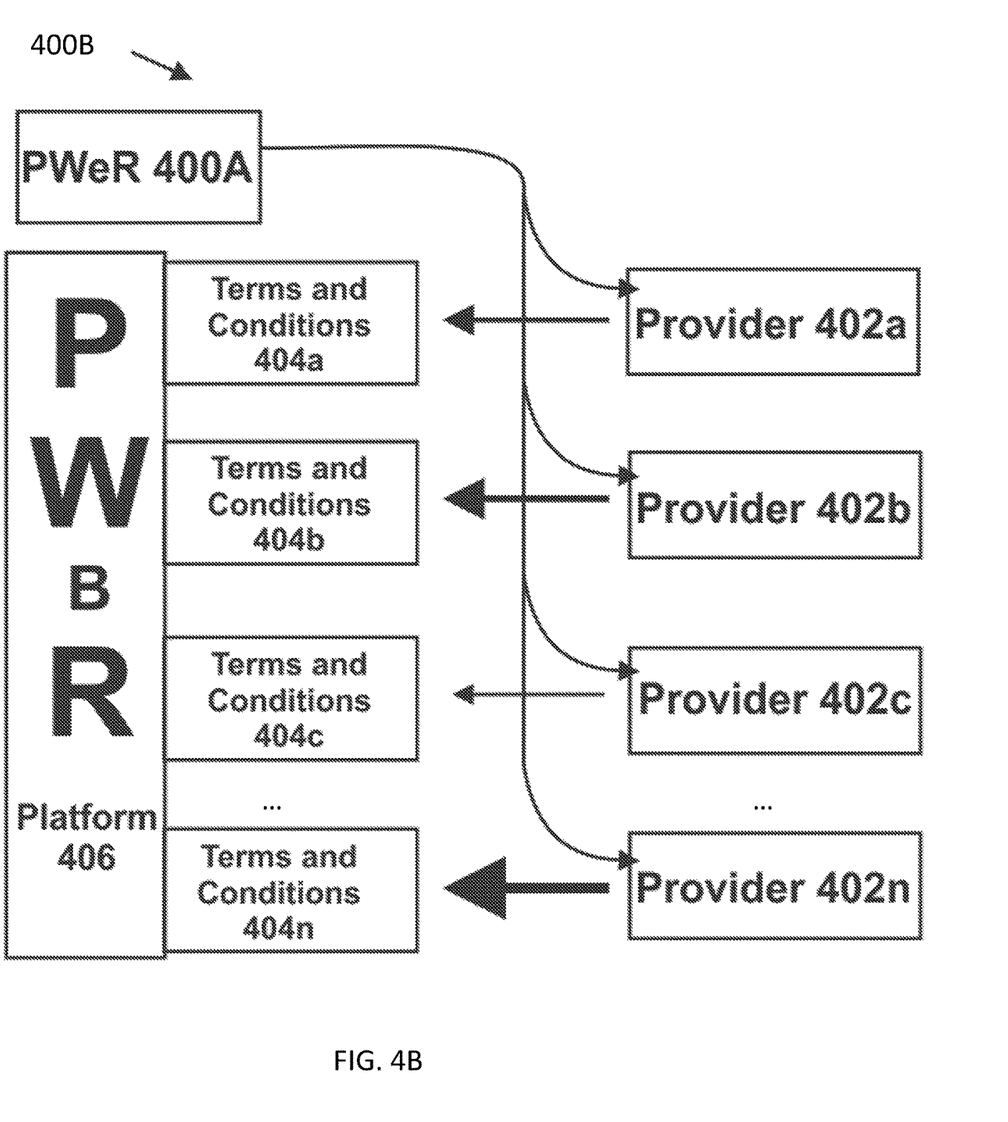
FIG. 4B shows another exemplary implementation of the methodology of FIG. 3, according to an embodiment of the present disclosure.

FIG. 4B shows another exemplary system 400B implementing the methodology of FIG. 3, according to an embodiment of the present disclosure. System 400B is a version of system 100B, modified according to the present disclosure. As shown in FIG. 4B, providers 482a, 482b, 482c . . . 482n can initiate transactions with research organizations 484a, 484b, 484c . . . 484n. The exchange of data and any corresponding payment can be monitored by both system 400A and an intermediary organization platform 486. Platform 486 can be analogous to platform 112 of FIG. 1B. The hybrid approach of FIG. 4B with the systems of the prior art increases the interoperability of the present disclosure.

Altogether, the present disclosure provides systems and methods to handle a large variance in data traffic where multiple providers are providing data and multiple requesters are requesting data. The security of the Blockchain ensures the secure exchange large volumes of data while ensuring patient privacy and maintaining data integrity. Additionally, the present disclosure provides data customers with timely, location-independent, internet-based service. Therefore, the present disclosure provides substantial benefits over conventional systems.

EXAMPLES

In a first exemplary implementation of the disclosed systems & methods, a patient/user/consumer can be a 60-year old woman, living in Florida; in overall fair health, but with some long-term chronic conditions. The woman is overweight, has high blood pressure, and has survived two types of cancer (melanoma and breast cancer). The woman is on several medications to manage her conditions. The woman registers, according to system 400A as discussed above with respect to FIG. 4A, and enters her basis demographics. She authorizes the upload of current information from her doctors by authorizing access to her primary care electronic health record platform. Her doctors can correspond to provider 428 as shown in FIG. 4A. The disclosed system aggregates her conditions, blood lab results, imaging reports, and conventional healthcare codes, along with other relevant information that may be available, such as, for example, doctor's notes.

Simultaneously, a medical researcher at a university is looking for historical information on women with certain conditions and who are also using certain prescription medications. The medical research can correspond to the accredited user 414 of FIG. 4A. In a major data search, the medical researcher identifies 100 women that meet their criteria. A remote computing device, such as device 404 of FIG. 4A, advises a cost of the data based on the total query made. For example, the queried data can cost a particular amount and correspond to the identified data 416 for some associated consumers 408. When the medical researcher agrees on the fee, the transaction is processed via the Blockchain. The medical researcher pays in tokens after buying the tokens at market price, for example, from a $3^{rd}$ party cryptocurrency exchange 410 of FIG. 4A.

The smart contract makes the transaction work, as the tokens are transferred from the medical researcher to the remote computing device, and from the remote computing device, via the Blockchain, to the women in the group in accordance with the pricing structure agreed upon. This first implementation shows that the consumers have no involvement or interaction regarding a price determination. After the transaction, the woman can receive a list of who has their de-identified information and what they were paid for it.

In some embodiments of this implementation, the medical researcher requests updated information at the end of one year or at a specific future date for the same patients. The remote computing device 404 can keep track of previous requests and offer a discounted rate for the updated files.

In a second exemplary implementation of the disclosed systems and methods, a researcher's (or any party who requests access to the health records) computing is done by proxy on identifiable data on a server with a closed perimeter. The researcher receives de-identified results. External users operate the remote computing device to perform searches and other logical processes but cannot actually see identified data; rather the researcher only sees the de-identified results of their query.

In a third exemplary implementation of the disclosed systems and methods, a lawyer defending in a food additive lawsuit wants to know how many patients nationally, who are less than 50 lbs. overweight, with high-density lipoprotein cholesterol below 70 and low-density lipoprotein above 120, (1) have blood pressures in a specific range, (2) contain a specific gene, and (3) consume a Mediterranean diet. The lawyer further queries, of that group, how many develop Type 2 diabetes and how does that relate statistically to the general population. The lawyer wishes to research whether there is (1) a correlation to the use of the food additive that is only sold regionally, and/or (2) a correlation to any other factor or metric. The lawyer can further examine how large a group of identifiable data is required, until the results do not yield identifiable information. These inquiries can be answered via the disclosed systems and methods.

In a fourth exemplary implementation of the disclosed systems and methods, a healthcare community in a region is composed of researchers, hospitals, insurance companies, and healthcare districts. The present disclosure allows these parties to all become part of a networked common distributed leger. Each participant within the regional environment operates at an appropriate level of security, and the Blockchain database ensures integrity.

In a fifth exemplary implementation of the disclosed systems and methods, the present disclosure allows for automatic execution of contractual arrangements. This feature can be used by payers to negotiate coverage and preauthorization for care; this automation provides large cost savings and advantages to uniformity. In other examples, the present disclosure allows for provider credentialing and provider directories to implement distance medicine.

In a sixth exemplary implementation of the disclosed systems and methods, the present disclosure provides international use of the electronic health record, through the use of (1) common standards and (2) a single certification entity to validate these applications and ensure data integrity.

In a seventh exemplary implementation of the disclosed systems and methods, the present disclosure provides means for patients/consumers who want a copy of their records outside of uncertain institutional control, desire that their healthcare records be accessible across international borders, and want the records to be connected directly to the national healthcare infrastructure. This presents an advantage for those who travel for medical tourism, or who are traveling for a specific procedure to be performed in another country that cannot be accommodated in their home country due to limitations or cost.

In an eighth exemplary implementation of the disclosed systems and methods, the present disclosure provides a platform where users convert their electronic health record to a patient-controlled dataset. The dataset is then truly patient centric with a patient-controlled electronic healthcare record system. Insurance companies can use smart contracts in the Blockchain for customer and claims management. For example, this extends to Medicare, Medicaid, and the Veterans Association as well as proposed systems integration with private healthcare providers using Blockchain data.

In a ninth exemplary implementation of the disclosed systems and methods, the Blockchain is first controlled by patients, using smart devices authorizing "smart contracts." The patient will initially authorize input, output, and use of their personal health information for use by direct care providers, both in an identified format and de-identified, such as for research use.

In a tenth exemplary implementation of the disclosed systems and methods, a registry of all devices connected to an Internet of Things is another potential beneficial use of the disclosed Blockchain systems and methods. In some examples, the present disclosure provides for digitizing the transactions of veterans' monetary benefits, including, for example, pension and compensation. All this information can be pertinent to researchers, even when de-identified.

In an eleventh exemplary implementation of the disclosed systems and methods, record-keeping ability of the disclosed Blockchain systems in methods can be used in veteran's association hospitals to track a patient's hospital visit, with developments tracked in a ledger as a transaction.

In a twelfth exemplary implementation of the disclosed systems and methods, a system can be provided for which is secured and enclosed. This system can be impervious to influence from external computing devices; for example, the system can be completely offline. In some examples, the system can be an integrated circuit, which has no potential for intrusion or modification of states within the circuit.

In a thirteenth exemplary implementation of the disclosed systems and methods, a system can be provided for which includes a closed perimeter. This exemplary system can include less secure protection of the disclosed tokens and payments due to the perimeter protection. In some examples, this disclosed system allows higher speed transactions between the relevant parties due to the lower computing complexity required for the transactions.

Blockchain Implementation

Various systems and methods of the present disclosure are provided for with Blockchain Technology. In particular, methodology 300 of FIG. 3 and FIGS. 4A-4B can be implemented via variations of the Blockchain technology discussed herein, as would be readily apparent to one skilled in the art. Exemplary technical details are discussed herein, and can be used according to an embodiment of the present disclosure. Blockchain Technology provides a distributed ledger for records. By having Blockchain maintain a distributed leger, each individual piece of data has one owner; however, the piece of data exists in many locations and may be fully secured. Each piece of data contains encrypted summary, or "cryptographic hash," of the previous block to tie the blocks together logically. Existing record blocks may only be added to the chain, never removed, thereby ensuring the integrity of the data and traceability to its roots.

In greater detail, each block in the chain contains a cryptographic hash of the previous block, a timestamp, and transaction data (generally referred to as a "Merkle Tree" root hash). Therefore, the Blockchain is impervious to modification of the data by researchers or other outside parties. The present disclosure provides an open, distributed ledger records compensation between patient and research parties in an efficient, verifiable, and permanent manner. The process of verifying the transaction requires a minimum number of independent third-party confirmations. Future advances in technological performance, speed, and connectivity will reduce the time required for this verification process. Therefore, the integrity of the data is easily verified. This is extremely valuable when the data are also blocks in a chain.

A Blockchain record is valid only so long as its peer "group" agrees on the consistency between the multiple distributed copies of the same data. Data is often secured within the group. Any change to an individual block in the Blockchain flags an error and invalidates the chain. This, in turn, alerts all participants until the error or inconsistency is resolved. This digital version ensures that nothing can be hidden. Each user of the data has their own copy of the record and each can see all the other user's copies of the record and validating for themselves and thereby ensuring that all copies agree.

Blockchain data can be that of any record: commodity transactions, legal records, or their healthcare records. As each transaction occurs—and all parties agree to its details—the transaction is encoded into a block of digital data and uniquely signed or identified. Each block is connected to the one before and after it, creating an irreversible, immutable and unduplicatable chain. Blocks are chained together, preventing any block or series of blocks from being altered, and preventing a block from being inserted between two existing blocks. Therefore, data cannot be added to the Blockchain which is inconsistent with existing data.

In this manner, there is no master, central, trusted, custodian of data because the data is collectively monitored by all parties in a decentralized manner. In some embodiments of the present disclosure, the data can be a distributed ledger file system spread over many computing devices. This decentralized storage of data, enabled by Blockchain, removes the requirement for a central server and the security and network infrastructure that surrounds it. Within the system, linkage between identified and de-identified data can exist, so long as it does not escape the secure environment.

Additionally, embodiments of the present disclosure can be protected against the 51% attack. In a 51% attack, a malicious source attempts to change the history of the Blockchain, by controlling over 50% of the chain, and editing the chain. Such an attack could be successful because the chain created by the malicious source would have the most records, and would force other chains to become logically consistent with the malicious source chain.

However, the present disclosure contemplates that these attacks would be computationally unattainable in the various embodiments of the present disclosure, due to the compute power required. In another effort to present the 51% attack, the chain can be segregated into portions, where not all blocks are accessible outside the portion. Less than 50% of the total blocks can be available in any given portion. If less than 50% of the blocks were modified in the adjacent portion, the exploit can be detected, according to an embodiment of the present disclosure. This method can be extended in chains of portions, as bocks of data grew.

In another example of protecting the Blockchain, the blocks can be distributed to Bit Torrent Clients, with a Blockchain embedded in a torrent swarm.

Some embodiments of the present disclosure can provide for an inter-planetary file system (IPFS). IPFS aggregates concepts from torrents, hash functions, and Blockchain to provide a fast, compact, and secure file chain. IPFS is a content-addressable data peer-to-peer network, where a query statement is content addressed (as opposed to selecting data by the exact numeric Internet address).

Traditional Hyperlinks require a centralized Dynamic Name Server that converts the URL format to a numeric Internet Protocol address. Hash keys of subordinate files in hierarchically organized data can be combined to yield a common parent hash key. Therefore, IPFS provides for the authentication of data that is stored elsewhere, and requires only one copy of the redundant data for all parties to refer to. Non-redundant changes and updates can be stored locally.

IPFS systems provide for transferring data over hierarchical network structures, enabling a self-certifying file system because the file name is the hash key; this allows validation of the data when regenerating a hash key and comparing it to the file name. The origin of the data follows the data because the file contains the signature of the servers that created/modified the file. The integrity of the data survives encryption and decryption as it moves in and out of secure environments. Decentralized data can be validated by a Distributed Hash Table (DHT).

IPFS intrinsically has many of the attributes of Blockchain but alleviates one defect of Blockchain, called "Chain Block". In Chain Block, data must be appended, not removed. Therefore, the size of blocks grows dramatically as the number of files is multiplied by updates. IPFS eschews file duplication intrinsically, because it only requires modification of the hash key with modification of the data. Rather than rewriting the data of the entire block, only the changes are noted. The reduced record sizes due to only rewriting the changes also translates to reduced archive requirements. These smaller records also result in the faster transfer of files; thereby, reducing network delays.

IPFS creates a way to authenticate the data of the basic block (Merkle Tree) and allows the hash key to address a master copy of the basic block in a single location. This avoids a great deal of redundant data when thousands of blocks are chained together.

Throughput is minimized in IPFS because (1) content is shared, and (2) record sizes only include modifications and a new Hash key. Additionally, without a central server, doubling of throughput with in and out transfers for every transaction are avoided. This is especially useful in small scale implementations.

Therefore, according to the various embodiments of the present disclosure, either Blockchain or IPFS provides the foundation for a medical database. In some examples, Blockchain data is translated into IPFS format. IPFS and Blockchain can create a central depository with the patient acting as a central player to push and pull data. This exemplary system benefits the patient, providers, and payers, provides a HIPAA compliant reservoir of data, and supplies "de-identified" data to accredited users. In some examples, the system exists as an international database, compensating patients for the use of their data. Blockchain reduces operational costs compared to conventional systems, increases digital security, and provides instantaneous updates.

Computer and Hardware Implementation

Figure 5:
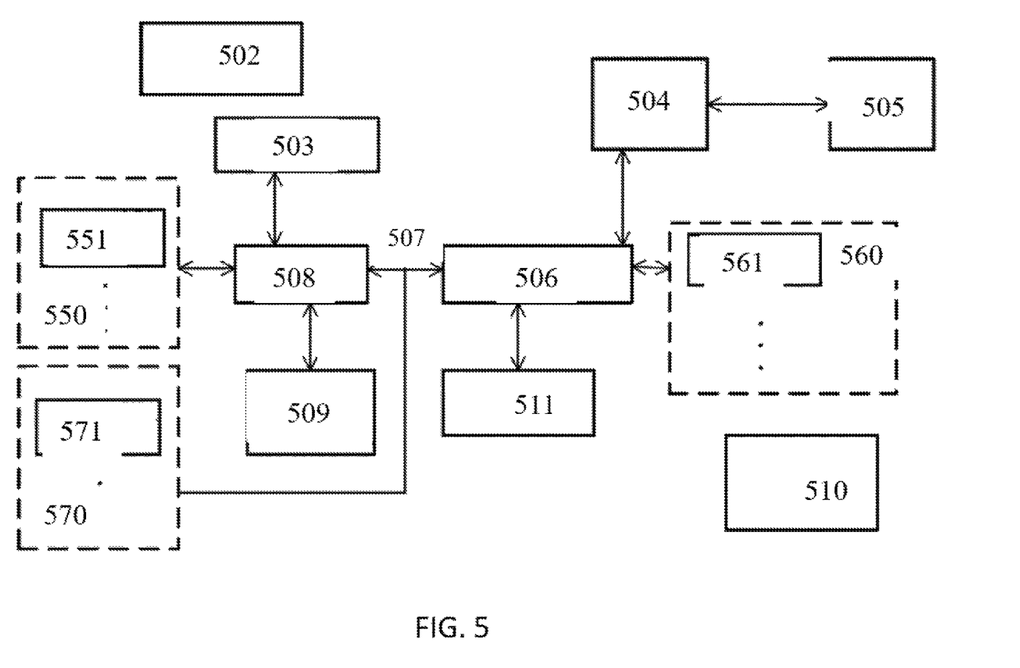
FIG. 5 is a schematic block diagram illustrating an exemplary system, in accordance with an implementation of the present disclosure.

FIG. 5 is a schematic block diagram illustrating an exemplary server system 500, in accordance with an implementation of the present disclosure. In this example, the server system 500 includes at least one microprocessor or processor 504; a BMC 503; one or more cooling modules 560; a main memory (MEM) 511; at least one power supply unit (PSU) 502 that receives an AC power from an AC power supply 501, and provides power to various components of the server system 500, such as the processor 504, north bridge (NB) logic 506, PCIe slots 560, south bridge (SB) logic 508, storage device 509, ISA slots 550, PCI slots 570, and BMC 503.

After being powered on, the server system 500 is configured to load software application from memory, a computer storage device, or an external storage device to perform various operations. The storage device 509 is structured into logical blocks that are available to an operating system and applications of the server system 500. The storage device 509 is configured to retain server data even when the server system 500 is powered off.

In FIG. 5, the memory 511 is coupled to the processor 504 via the NB logic 506. The memory 511 may include, but is not limited to, dynamic random access memory (DRAM), double data rate DRAM (DDR DRAM), static RAM (SRAM), or other types of suitable memory. The memory 511 can be configured to store firmware data of the server system 500. In some configurations, firmware data can be stored on the storage device 509.

In some implementations, the server system 500 can further comprise a flash storage device. The flash storage device can be a flash drive, a random access memory (RAM), a non-volatile random-access memory (NVRAM), or an electrically erasable programmable read-only memory (EEPROM). The flash storage device can be configured to store system configurations such as firmware data.

The processor 504 can be a central processing unit (CPU) configured to execute program instructions for specific functions. For example, during a booting process, the processor 504 can access firmware data stored in the BMC 503 or the flash storage device, and execute the BIOS 505 to initialize the server system 500. After the booting process, the processor 504 can execute an operating system in order to perform and manage specific tasks for the server system 500.

In some configurations, the processor 504 can be multi-core processors, each of which is coupled together through a CPU bus connected to the NB logic 506. In some configurations, the NB logic 506 can be integrated into the processor 504. The NB logic 506 can also be connected to a plurality of peripheral component interconnect express (PCIe) slots 560 and an SB logic 508 (optional). The plurality of PCIe slots 560 can be used for connections and buses such as PCI Express x1, USB 2.0, SMBus, SIM card, future extension for another PCIe lane, 1.5 V and 3.3 V power, and wires to diagnostics LEDs on the server system 500's chassis.

In system 500, the NB logic 506 and the SB logic 508 are connected by a peripheral component interconnect (PCI) Bus 507. The PCI Bus 507 can support functions on the processor 504 but in a standardized format that is independent of any of the processor 504's native buses. The PCI Bus 507 can be further connected to a plurality of PCI slots 570 (e.g., a PCI slot 571). Devices connect to the PCI Bus 507 may appear to a bus controller (not shown) to be connected directly to a CPU bus, assigned addresses in the processor 504's address space, and synchronized to a single bus clock. PCI cards that can be used in the plurality of PCI slots 570 include, but are not limited to, network interface cards (NICs), sound cards, modems, TV tuner cards, disk controllers, video cards, small computer system interface (SCSI) adapters, and personal computer memory card international association (PCMCIA) cards.

The SB logic 508 can couple the PCI Bus 507 to a plurality of expansion cards or ISA slots 550 (e.g., an ISA slot 551) via an expansion bus. The expansion bus can be a bus used for communications between the SB logic 508 and peripheral devices, and may include, but is not limited to, an industry standard architecture (ISA) bus, PC/504 bus, low pin count bus, extended ISA (EISA) bus, universal serial bus (USB), integrated drive electronics (IDE) bus, or any other suitable bus that can be used for data communications for peripheral devices.

In this example, BIOS 505 can be any program instructions or firmware configured to initiate and identify various components of the server system 500. The BIOS is an important system component that is responsible for initializing and testing hardware components of a corresponding server system. The BIOS can provide an abstraction layer for the hardware components, thereby providing a consistent way for applications and operating systems to interact with a peripheral device such as a keyboard, a display, and other input/output devices.

In system 500, the SB logic 508 is further coupled to the BMC 503 that is connected to the PSU 502. In some implementations, the BMC 503 can also be a rack management controller (RMC). The BMC 503 is configured to monitor operation status of components of the server system 500, and control the server system 500 based upon the operation status of the components.

Although only certain components are shown within the exemplary systems 500 in FIG. 5, various types of electronic or computing components that are capable of processing or storing data, or receiving or transmitting signals, can also be included in the exemplary system 500. Further, the electronic or computing components in the exemplary system 500 can be configured to execute various types of application, and/or can use various types of operating systems. These operating systems can include, but are not limited to, Android, Berkeley Software Distribution (BSD), iPhone OS (iOS), Linux, OS X, Unix-like Real-time Operating System (e.g., QNX), Microsoft Windows, Window Phone, and IBM z/OS.

Depending on the desired implementation for the exemplary systems 500, a variety of networking and messaging protocols can be used, including but not limited to TCP/IP, open systems interconnection (OSI), file transfer protocol (FTP), universal plug and play (UpnP), network file system (NFS), common internet file system (CIFS), AppleTalk etc. As would be appreciated by those skilled in the art, FIG. 5 is used for purposes of explanation. Therefore, a network system can be implemented with many variations, as appropriate, yet still provide a configuration of network platform in accordance with various examples of the present disclosure.

In exemplary configurations of FIG. 5, the exemplary system 500 can also include one or more wireless components operable to communicate with one or more electronic devices within a computing range of the particular wireless channel. The wireless channel can be any appropriate channel used to enable devices to communicate wirelessly, such as Bluetooth, cellular, NFC, or Wi-Fi channels. It should be understood that the device can have one or more conventional wired communications connections, as known in the art. Various other elements and/or combinations are possible as well within the scope of various examples.

While various examples of the present invention have been described above, it should be understood that they have been presented by way of example only, and not limitation. Numerous changes to the disclosed examples can be made in accordance with the disclosure herein without departing from the spirit or scope of the invention. Thus, the breadth and scope of the present invention should not be limited by any of the above described examples. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular examples only and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. Furthermore, terms, such as those defined in commonly used dictionaries, should be interpreted as having a meaning that is consistent with their meaning in the context of the relevant art, and will not be interpreted in an idealized or overly formal sense unless expressly so defined herein.

What is claimed is:

1. A method for securely transmitting electronic healthcare records between a plurality of computing devices in communication with each other, comprising:
   receiving, at a first computing device, a request from a second computing device to access at least one electronic health record in a database of electronic health records, wherein the request from the second computing device is based on accessing de-identified data of the at least one electronic health record, wherein the database of electronic health records is stored at a remote memory module, wherein the database of electronic health records comprises de-identified data accessible by the plurality of computing devices;
   sending, from the first computing device, at least one authorization requirement to the second computing device;
   detecting, at the first computing device, that the at least one authorization requirement has been provided by the second computing device;
   based on detecting that the at least one authorization requirement has been provided, generating, at the first computing device, a token associated with the at least one authorization requirement and the received request, wherein the token provides a decryption key for the encrypted identifiable data,
   wherein the token corresponds to a block in a Blockchain, the block including a cryptographic hash of a previous block, a timestamp, and transaction data related to the received request and the at least one authorization requirement;
   retrieving, by the first computing device, identifiable data from the remote memory module, wherein the identifiable data corresponds to the received request;
   encrypting, by the first computing device, the identifiable data;
   sending the token to the second computing device from the first computing device to access the at least one electronic health record; and
   sending, from the first computing device, the encrypted identifiable data to the second computing device.

2. The method of claim 1, wherein the at least one authorization requirement comprises a payment request based on the received request.

3. The method of claim 2, wherein detecting that the at least one authorization requirement has been provided comprises:
receiving, at the first computing device, a payment from the second computing device, wherein the payment corresponds to the payment request.

4. The method of claim 3, wherein the method further comprises sending, via the first computing device, the payment to a user associated with the at least one electronic health record.

5. The method of claim 1, wherein each electronic health record in the database of electronic health records is automatically generated upon receiving health information from a user.

6. The method of claim 5, wherein generating each electronic health record is based on the received health information and comprises access restrictions.

7. A system for securely transmitting electronic healthcare records between a plurality of computing devices in communication with each other, comprising:
one or more processors; and
a memory coupled to the processors comprising instructions executable by the processors, the processors being operable when executing the instructions to:
receive, at a first computing device, a request from a second computing device to access at least one electronic health record in a database of electronic health records, wherein the request from the second computing device is based on accessing de-identified data of the at least one electronic health record, wherein the database of electronic health records is stored at a remote memory module, wherein the database of electronic health records comprises de-identified data accessible by the plurality of computing devices;
send, from the first computing device, at least one authorization requirement to the second computing device;
detect, at the first computing device, that the at least one authorization requirement has been provided by the second computing device;
based on detecting that the at least one authorization requirement has been provided, generate, at the first computing device, a token associated with the at least one authorization requirement and the received request, wherein the token provides a decryption key for the encrypted identifiable data,
wherein the token corresponds to a block in a Blockchain, the block including a cryptographic hash of a previous block, a timestamp, and transaction data related to the received request and the at least one authorization requirement;
retrieve, by the first computing device, identifiable data from the remote memory module, wherein the identifiable data corresponds to the received request;
encrypt, by the first computing device, the identifiable data;
send the token to the second computing device from the first computing device to access the at least one electronic health record; and
send, from the first computing device, the encrypted identifiable data to the second computing device.

8. The system of claim 7, wherein the at least one authorization requirement comprises a payment request based on the received request.

9. The system of claim 8, wherein detecting that the at least one authorization requirement has been provided comprises:
receiving, at the first computing device, a payment from the second computing device, wherein the payment corresponds to the payment request.

10. The system of claim 9, wherein executing the instructions further comprises:
send, via the first computing device, the payment to a user associated with the at least one electronic health record.

11. The system of claim 7, wherein each electronic health record in the database of electronic health records is automatically generated upon receiving health information from a user.

12. The system of claim 11, wherein generating each electronic health record is based on the received health information and comprises access restrictions.

* * * * *